US009931060B2

(12) United States Patent
Connolly et al.

(10) Patent No.: US 9,931,060 B2
(45) Date of Patent: Apr. 3, 2018

(54) SYSTEM AND METHOD FOR MEASURING FEMALE URETHRAL LENGTH

(71) Applicant: Personal Medical Corp., Redmond, WA (US)

(72) Inventors: Kevin M. Connolly, Newton, MA (US); Sagi Brink-Danan, Providence, RI (US)

(73) Assignee: Personal Medical Corp., Redmond, WA (US)

( * ) Notice: Subject to any disclaimer, the term of this patent is extended or adjusted under 35 U.S.C. 154(b) by 273 days.

(21) Appl. No.: 14/505,633

(22) Filed: Oct. 3, 2014

(65) Prior Publication Data
US 2015/0099999 A1    Apr. 9, 2015

Related U.S. Application Data

(60) Provisional application No. 61/886,418, filed on Oct. 3, 2013.

(51) Int. Cl.
*A61B 5/107* (2006.01)
*A61B 5/20* (2006.01)
*A61B 5/00* (2006.01)

(52) U.S. Cl.
CPC ............ *A61B 5/1076* (2013.01); *A61B 5/202* (2013.01); *A61B 5/6874* (2013.01); *A61M 2210/1089* (2013.01); *A61M 2210/1092* (2013.01); *A61M 2210/1096* (2013.01)

(58) Field of Classification Search
CPC .. A61M 2210/1089; A61M 2210/1092; A61M 2210/1096; A61B 5/1076; A61B 5/6874; A61B 5/202
See application file for complete search history.

(56) References Cited

U.S. PATENT DOCUMENTS 5,171,248 A * 12/1992 Ellis ..................... A61B 17/921
                                                              33/512
5,657,764 A *  8/1997 Coulter ................ A61B 5/1076
                                                              600/591
(Continued)

FOREIGN PATENT DOCUMENTS

WO         WO 0176468 A1 * 10/2001 ........... A61B 5/1076

OTHER PUBLICATIONS

Tube. (1992). In C. G. Morris (Ed.), Academic Press Dictionary of Science and Technology (4th ed.). Oxford, UK: Elsevier Science & Technology. Retrieved from http://search.credoreference.com/content/entry/apdst/tube/0.*

*Primary Examiner* — David J McCrosky
(74) *Attorney, Agent, or Firm* — Cesari and McKenna, LLP

(57) ABSTRACT

In one embodiment, a device measures the length of the urethra. The device includes a hollow tube having markings, wherein the hollow tube includes an internal end and an external end. The internal end includes one or more fins that can be manipulated into an open position and a closed position. The external end includes an opening allowing the insertion of a push-tube sliding axially within the body of the hollow tube, the push-tube being used to manipulate the fins into the open and closed positions. Further, an outer ring moves axially along the exterior of hollow tube and is utilized to measure the length of the urethra.

15 Claims, 2 Drawing Sheets

(56) References Cited

U.S. PATENT DOCUMENTS

| | | | |
|---|---|---|---|
| 6,527,737 B2 * | 3/2003 | Kaneshige | A61M 25/0017 604/104 |
| 6,565,536 B1 * | 5/2003 | Sohn | A61M 25/0074 128/DIG. 26 |
| 8,715,244 B2 * | 5/2014 | Prechtel | A61M 39/0247 604/175 |
| 9,061,121 B2 * | 6/2015 | Galloway | A61B 17/3403 |
| 2010/0185155 A1 * | 7/2010 | McMichael | A61J 15/0065 604/175 |

* cited by examiner

SYSTEM AND METHOD FOR MEASURING FEMALE URETHRAL LENGTH

CROSS-REFERENCE TO RELATED APPLICATIONS

The present application claims the benefit of U.S. Provisional Patent Application Ser. No. 61/886,418, which was filed on Oct. 3, 2013, by Connolly et al. for a SYSTEM AND METHOD FOR MEASURING FEMALE URETHRAL LENGTH and is hereby incorporated by reference.

BACKGROUND OF THE INVENTION

Field of the Invention

This invention relates to a device and method for measuring the length of the female urethra.

Background Information

A variety of devices exist to assist patients in achieving improved urinary control and voiding, including different types of passive and active plugs, inserts, catheters, pumps and others.

Many of these devices, in order to achieve an optimal—or even an acceptable—level of performance, safety and comfort require accurate measuring—or sizing—of the urethral length. The urethral length is most often defined as the distance from the neck of the urinary bladder to the external meatus.

SUMMARY OF THE INVENTION

In one embodiment, a device measures the length of the urethra, and specifically, the length from the bladder neck to the meatus. The device includes a hollow tube (e.g., catheter) having markings, wherein the hollow tube includes an internal end and an external end. The internal end includes one or more fins that can be manipulated into an open position having a larger diameter and a closed position having a smaller diameter. The external end includes an opening allowing the insertion of a push-tube sliding axially within the body of the hollow tube, the push-tube being used to manipulate the fins into the open and closed positions. Further, an outer ring moves axially along the exterior of hollow tube, and a guard may be positioned on the exterior of the hollow tube to prevent the device from accidentally sliding fully into the urethra/bladder.

In operation, the ring is positioned at the guard, and the internal end of the hollow tube is placed into the urethra until the ring pushes against the meatus of a patient, for example. The hollow tube is sufficiently long that the internal end extends within the patient's bladder. A pusher-and-grabber mechanism may then be utilized, in a syringe-like fashion, to push the push-tube from the external end to the internal end of the hollow tube, thus causing the fins to open. The hollow tube may then be pulled outwardly, for example, by a physician or person utilizing the device, until the now open fins rest against the bladder neck. The ring is pushed along the tube towards the internal end until the ring rests against the meatus of the patient. The position of the ring relative to the internal end of the hollow tube indicates the length of the urethra. Specifically, the position of the ring at a specific marking on the hollow tube indicates the length of the urethra.

BRIEF DESCRIPTION OF THE DRAWINGS

The description below refers to the accompanying drawings, of which.

DETAILED DESCRIPTION OF AN ILLUSTRATIVE EMBODIMENT

Figure 1:
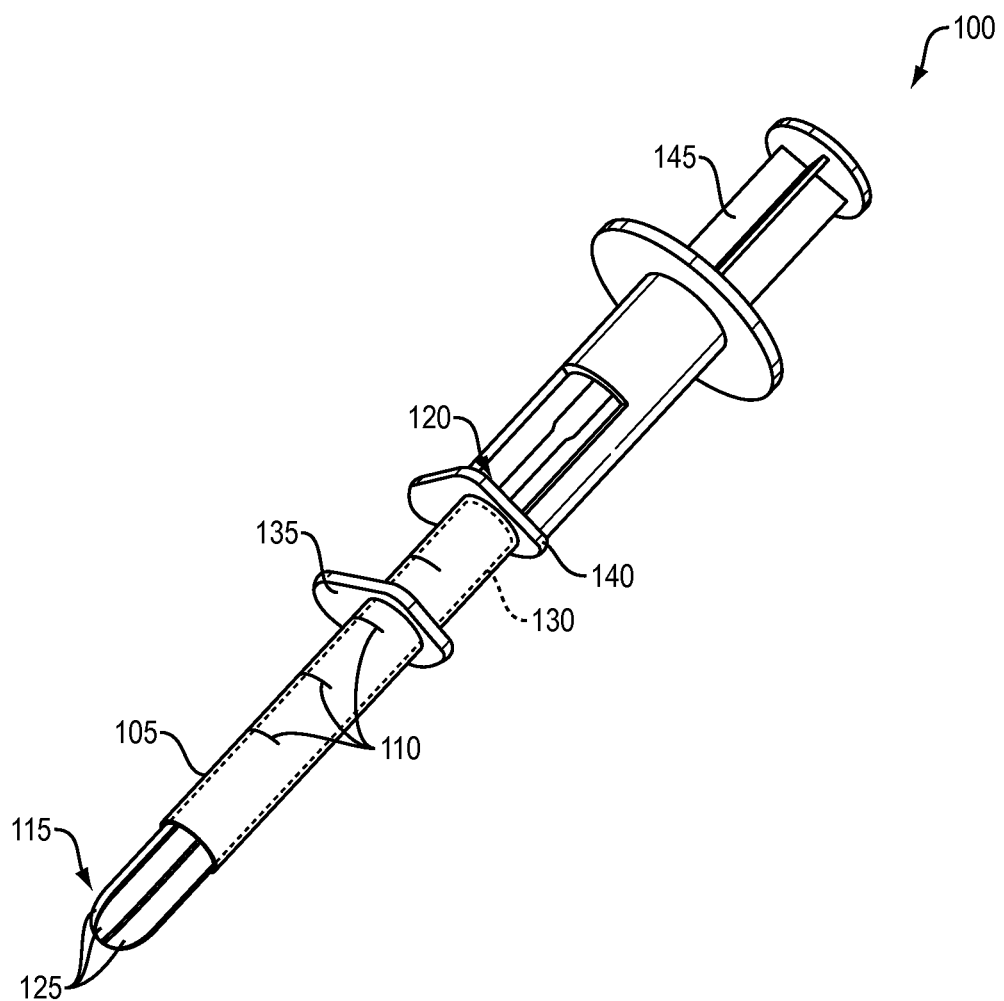
FIG. 1 is an example device for measuring the length of the urethra.

FIG. 1 is an example device 100 for measuring the length of the urethra, for example, from the bladder neck to the meatus. Device 100 includes a hollow tube 105 with markings 110. The hollow tube 105 has an internal end 115 and an external end 120, wherein the internal end may be placed into the urethra of a patient, for example. The internal end 115 includes one or more fins 125 that may be in a closed position for insertion and extraction (as shown) or in an open position (not shown) for urethral measurement. The markings 110 may indicate for example, a distance each marking is from the internal end 115 of the hollow tube 105. The hollow tube 105, for example, may be a catheter.

The external end 120 has an opening so that a push-tube 130 may be placed within the hollow tube 105. The push-tube 130 slides axially within the hollow tube 105 to manipulate the one or more fins 125. Specifically, when the push-tube 130 slides axially from the external end 125 to the internal end 115, the one or more fins 125 may be pushed outwardly to the open position. Advantageously, the push-tube 130 prevents bodily fluids, such as urine, from entering the hollow tube 105. Conversely, the one or more fins 125 may be in the closed position when the push-tube 130 remains at the external end 120 of the hollow tube 105. Advantageously, the one or more fins 125 that are closed prevent bodily fluids, such as urine, from entering the hollow tube 105.

Outer ring 135 may be placed on the exterior of hollow tube 105. The outer ring 135 is movable axially along the exterior portion of the hollow tube 105. The outer ring 135 may be made from a flexible material so as to not lose its position on the exterior of the hollow tube 105, but is also moveable on the exterior of the hollow tube 105 by, for example, an operator pushing or pulling the outer ring 135. Further, outer ring 135 may be of an enlarged cross-section allowing the operator, for example, to easily move the outer ringer 135 on the exterior of the hollow tube 105. Guard 140 may also reside on the exterior of the hollow tube 105 to prevent the hollow tube 105 from accidentally sliding fully into the urethra/bladder.

A pusher-and-grabber mechanism 145 may be utilized to move the push-tube 130 from the external end 120 to the internal end 115 to push the fins 115 in an outward manner and into the open position. For example, the pusher-and-grabber mechanism 145 may behave similarly to a syringe and allow an operator to apply pressure to pusher-and-grabber mechanism 145 to move the push-tube 130 through the hollow tube 105 and to the internal end 115 of the hollow tube 105. When the push-tube 130 reaches the one or more fins 115 at the internal end 115 of the hollow tube 105, the fins 125 will be pushed outwardly to its open position.

Figure 2:
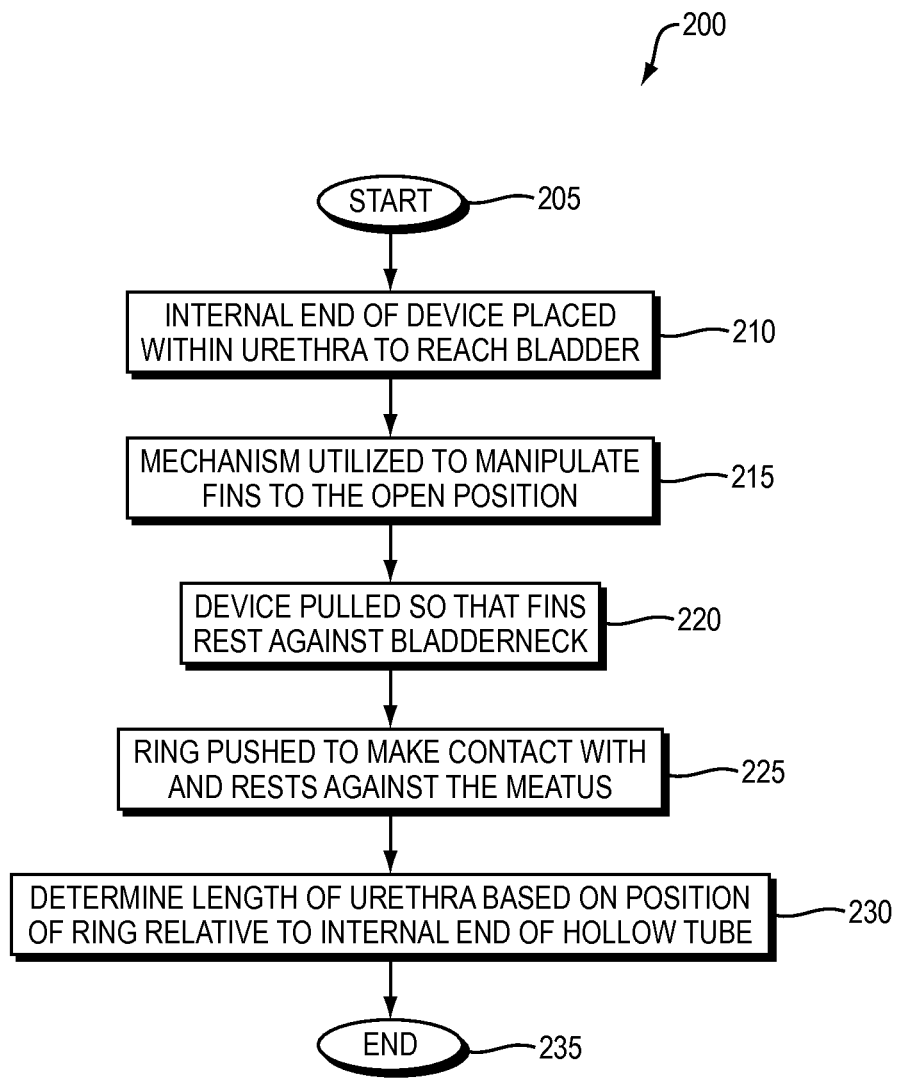
FIG. 2 is an example procedure for measuring the length of the urethra utilizing the device of FIG. 1.

FIG. 2 is an example procedure for measuring the length of the urethra utilizing the device of FIG. 1. The procedure 200 starts at step 205 and continues to step 210, where the internal end of the device, as described in FIG. 1, is placed within a urethra. For example, the internal end of the device may be placed within the urethra until the outer ring of the device, which is positioned at the guard, pushes up against the meatus. The hollow tube of the device is sufficiently long that the internal end of the hollow tube rests within the bladder. At step 215, the pusher-and-grabber mechanism may be utilized to manipulate the fins, at the internal end, to the open position. For example, an operator may apply pressure to the pusher-and-grabber mechanism causing the push-tube to travel within the hollow tube and towards the internal end to manipulate the fins to the open position. At step 220, the device may be pulled, slightly, by the operator, so that the fins rest against the bladder neck. At step 225, the outer ring may be pushed along the tube towards the internal end until the ring makes contact with and rests against the meatus. As step 230, the length of the urethra, from the bladder neck to the meatus, is determined based on the position of the ring relative to the internal end of the hollow tube of the device. Specifically, the position of the ring relative to the internal end of the hollow tube indicates the length of the urethra and may be indicated based upon the ring being located at a marking on the hollow tube. For example, a specific marking may indicate that the distance from the specific marking to the internal end of the hollow tube is 1.5 inches. Thus, if the ring is positioned at that marking, this would indicate that the length of the urethra is 1.5 inches. At step 235, the procedure ends. The measurement may also or instead be determined after the device is removed, by pulling the push-tube to allow the fins to move to the closed position such that the device may be removed from the body, with the position of the ring on the device indicating the measurement.

The foregoing description described certain example embodiments. It will be apparent, however, that other variations and modifications may be made to the described embodiments, with the attainment of some or all of their advantages. Accordingly, the foregoing description is to be taken only by way of example, and not to otherwise limit the scope of the disclosure.

What is claimed is:

1. A device to measure a length of a urethra, comprising:
   a hollow tube having an internal end and external end, wherein the hollow tube is sufficiently long enough to be placed in the urethra and reach a bladder;
   one or more fins located at the internal end of the hollow tube, wherein the one or more fins are in a closed position or an open position;
   a push-tube positioned within the hollow tube at the external end, the push-tube configured to slide axially within the hollow tube;
   a push-grabber configured to push the push-tube from the external end to the internal end of the hollow tube to cause the fins, located at the internal end, to move from the closed position to the open position, wherein the fins rest on a neck of the bladder and wherein the push-tube prevents fluid from entering the hollow tube when the push-tube is at the internal end; and
   an outer ring on an exterior of the hollow tube utilized to determine the length of the urethra, wherein a distance from a point on the exterior where the outer ring is located to the one or more fins is the length of the urethra after the fins have moved from the closed position to the open position to rest on the neck of the bladder.

2. The device of claim 1, wherein the pusher-grabber is configured to receive pressure to push the push-tube from the external end to the internal end.

3. The device of claim 1, wherein the hollow tube includes one or more markings indicating a distance each marking is from the internal end.

4. The device of claim 1, wherein the fluid includes at least urine.

5. The device of claim 1, wherein the one or more fins are in the closed position when the push-tube is at the external end.

6. The device of claim 1, wherein the outer ring is configured to move axially along the exterior of the hollow tube.

7. The device of claim 1, further comprising a guard residing on the exterior of the hollow tube, where the guard prevents the hollow tube from sliding fully into the urethra.

8. The device of claim 1, wherein the push-tube is configured to have a size and shape, wherein the size and shape of the push-tube prevent fluid from entering the hollow tube when the push-tube is at the internal end.

9. A device comprising:
   a tube having an internal end and an external end;
   one or more fins located at the internal end;
   a push-tube positioned within the tube and configured to move between the external end and the internal end;
   a push-grabber configured to move the push-tube from the external end to the internal end causing the fins to go from a closed position to an open position to rest on a bladder neck, wherein the push-tube prevents fluid from entering the tube when the push-tube is at the internal end; and
   a ring configured to slide on an exterior portion of the tube, where a distance from the ring to the internal end indicates a length of a urethra when the device is placed in the urethra and after the fins have moved from the closed position to the open position to rest on the bladder neck.

10. The device of claim 9, wherein the pusher-grabber is configured to receive pressure to push the push-tube from the external end to the internal end.

11. The device of claim 9, wherein the tube includes one or more markings indicating a distance each marking is from the internal end.

12. The device of claim 9, wherein the fluid is at least urine.

13. The device of claim 9, wherein the one or more fins are in the closed position when the push-tube is at the external end and transitions to the open position when the push-tube moves to the internal end.

14. The device of claim 9, wherein the outer ring is configured to move axially along the exterior portion of the tube.

15. The device of claim 9, further comprising a guard configured to reside on the exterior portion of the tube, the guard further configured to prevent the tube from sliding fully into the urethra.

* * * * *